United States Patent [19]
Gerard

[11] Patent Number: 5,388,444
[45] Date of Patent: Feb. 14, 1995

[54] APPARATUS AND METHODS FOR DETERMINING REQUIRED VACUUM CHARACTERISTICS OF A RADON EVACUATION SYSTEM

[76] Inventor: Thomas J. Gerard, N. 1322 Post St., Spokane, Wash. 99201

[21] Appl. No.: 132,761

[22] Filed: Oct. 6, 1993

[51] Int. Cl.⁶ .................... F24F 7/007; G01N 15/08
[52] U.S. Cl. .......................................... 73/37; 73/38; 454/341; 454/909
[58] Field of Search ................. 73/37, 38; 454/341, 454/339, 344, 909

[56] References Cited

U.S. PATENT DOCUMENTS

| | | | |
|---|---|---|---|
| 4,747,311 | 5/1988 | Hojoh | 73/702 |
| 4,885,984 | 12/1989 | Franceus | 98/42.02 |
| 4,945,771 | 8/1990 | Ogden | 73/861.58 |
| 5,131,887 | 7/1992 | Traudt | 454/255 |
| 5,167,366 | 12/1992 | Desmarais et al. | 236/49.3 |

OTHER PUBLICATIONS

Mosley et al. "Application of Radon Reduction Methods", EPA/625/5-88/024, Aug. 1988, pp. 34-36, 41-43, 49-51.

Primary Examiner—Hezron E. Williams
Assistant Examiner—Michael J. Brock
Attorney, Agent, or Firm—Wells, St. John, Roberts, Gregory & Matkin

[57] ABSTRACT

Testing apparatus and methods are described for determining required vacuum characteristics of a radon evacuation system, wherein the radon evacuation system is of a type which utilizes floor vent holes in a basement floor to evacuate radon from beneath the basement floor. The preferred embodiment comprises an elongated vacuum tube extending from a floor vent hole to a variable vacuum test source. Pressure and air velocity measurement devices are positioned to determine actual static pressure and air flow rate within the vacuum tube. To determine the minimum vacuum required at the floor vent hole, the vacuum test source is adjusted to produce the lowest vacuum which will maintain a negative pressure in nearby test holes. The corresponding static pressure and air flow rate are then noted from the measurement devices.

25 Claims, 7 Drawing Sheets

APPARATUS AND METHODS FOR DETERMINING REQUIRED VACUUM CHARACTERISTICS OF A RADON EVACUATION SYSTEM

TECHNICAL FIELD

This invention relates to methods and apparatus for determining the required or optimum capacity of blower systems which are used to evacuate radon from beneath basement floors.

BACKGROUND OF THE INVENTION

The presence of radon gas in residences and commercial buildings is now recognized as a health threat. Accordingly, significant commercial effort is dedicated to the fabrication and installation of systems for eliminating or removing radon gas from new and existing buildings.

It is generally recognized that radon is generated by decaying radium in the ground beneath buildings. Radon enters buildings through the floors or walls of their basements. Because of increasing efforts to conserve heating and cooling energy, many newer homes and buildings are relatively airtight. Such homes and buildings are particularly likely to contain unacceptable concentrations of radon.

Radon can be removed by venting a building's basement to the external atmosphere. Such venting is often facilitated by a fan, pump, or blower which is positioned to create a slightly negative pressure in the basement in comparison to the pressure of the atmosphere outside the building. This provides continuous removal of radon and other gases from the basement.

Rather than venting the basement itself, many radon evacuation systems are connected to vent gases from ground regions under the basement floor, rather than from the basement itself. Such systems are generally preferable since less air transfer is required. Furthermore, these systems vent the radon before it can enter the building.

It is relatively easy to provide for radon removal during construction of a home or commercial building. However, it has become necessary to retrofit existing structures with systems for eliminating the presence of radon. In fact, the design and installation of radon elimination systems for connection to underfloor ground regions of existing buildings has become a significant commercial activity. Nevertheless, determining the parameters of such radon elimination systems is largely a matter of guesswork. Accordingly, many systems provide much more capacity than actually needed. While this has no adverse effect on radon removal, the costs of operating an over-sized radon evacuation system can be very significant—especially in large commercial buildings. Accordingly, there is a need for devices and procedures for correctly sizing the components of radon removal systems.

Current underfloor radon removal systems typically comprise a blower or pump which is connected through one or more vent holes in a basement floor to underfloor ground regions beneath a building. Such vent holes typically have diameters in the range of about four inches. The number of vent holes is mandated by the available air or fluid communication beneath the basement floor. In some cases, a single, centrally-located vent hole may be sufficient to create a negative pressure (with regard to the building interior) beneath an entire basement floor. In other cases, underfloor features may prevent air or pressure communication between the location of the vent hole and other locations. Accordingly, multiple vent holes must be provided to create a negative pressure beneath the entire building floor. Testing must be conducted to determine the number of required vent holes.

Current testing methods involve drilling a number of test holes at various locations around a basement floor. Test holes are typically about three-eighths of an inch in diameter. Testing proceeds by first connecting a vacuum test source such as a pump or blower to a single larger vent hole. All other vent holes and test holes are sealed. The vacuum test source typically comprises a general-purpose shop-type vacuum cleaner or some other type of blower which operates at a fixed capacity.

A very sensitive pressure measuring or vacuum sensing device is then used to determine whether the vacuum test source is creating a negative pressure in nearby test holes (the terms "vacuum" and "negative pressure" are used in this document to indicate pressures below ambient or atmospheric pressure). If the vacuum test source does not create a vacuum or negative pressure in a particular test hole, an additional vent hole is provided in closer proximity to that particular test hole and the vacuum test source is connected to the additional vent hole to determine whether it will provide the needed negative pressure at the test hole. This testing continues, with additional vent holes being provided as needed so that each test hole is subjected to a negative pressure by at least one of the vent holes.

The procedure described above results in one or more vent holes which must be connected in parallel to a permanently-installed vacuum source. The permanently-installed vacuum source must be sized to subject all vent holes, simultaneously, to enough vacuum to put the entire underfloor region under a negative pressure with respect to the internal air pressure of the building. Currently, specifying the capacity of the permanently-installed vacuum source is done mostly by guesswork. Accordingly, the permanently-installed vacuum source is usually grossly oversized. In a large commercial building, the power consumed by the permanently-installed vacuum source is a significant expense. Therefore, it would be desirable to provide a permanently-installed vacuum source in a radon removal system which has a capacity of no more than is actually needed to provide a negative pressure at all underfloor areas.

The invention described below comprises methods and apparatus which can be used to determine the actual pressure and volume requirements of a permanently-installed vacuum source in a radon removal system such as described above.

DETAILED DESCRIPTION OF THE PREFERRED EMBODIMENT

Figure 1:
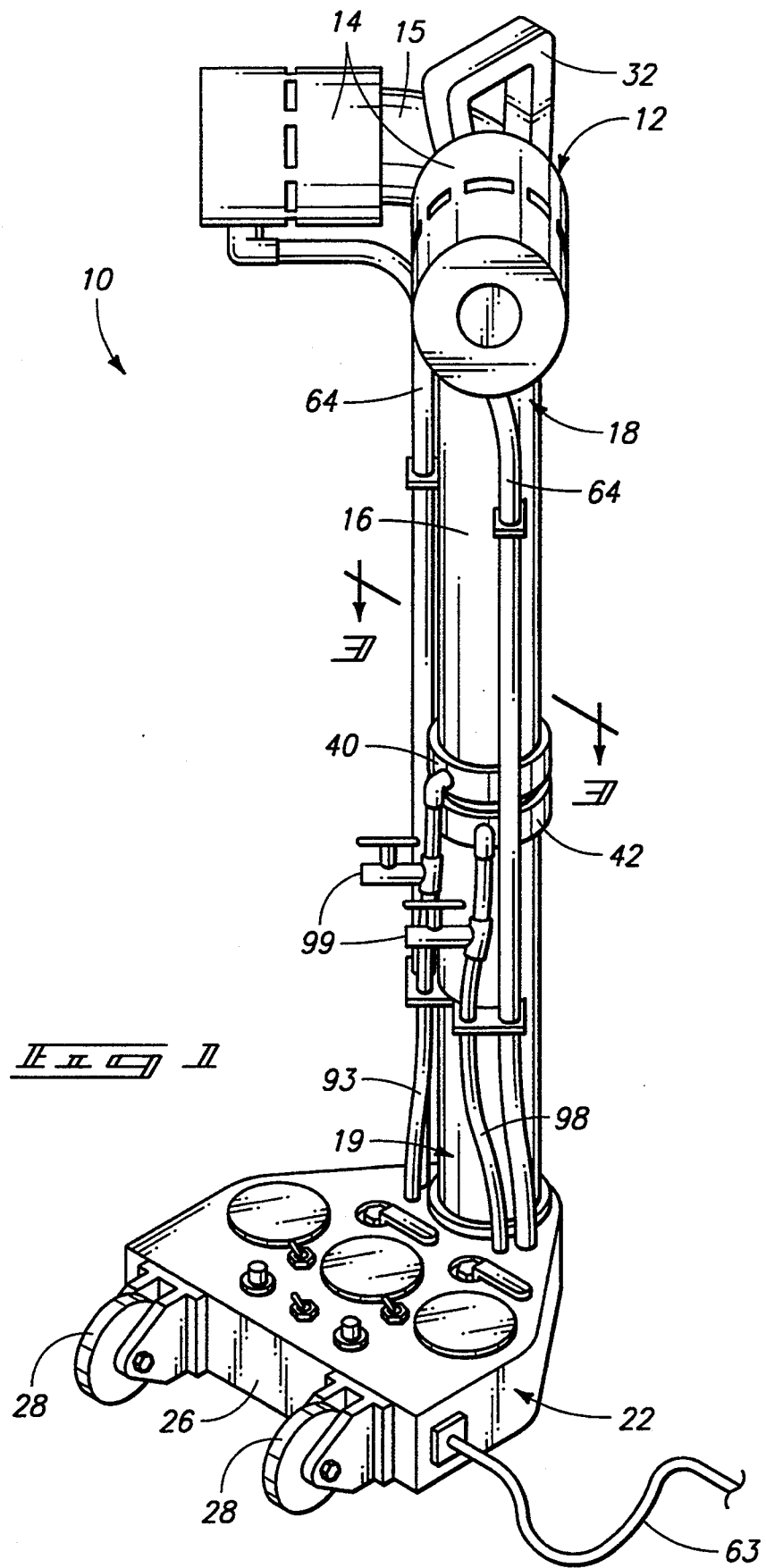
FIG. 1 is a perspective view of a testing apparatus in accordance with a preferred embodiment of the invention.
Figure 2:
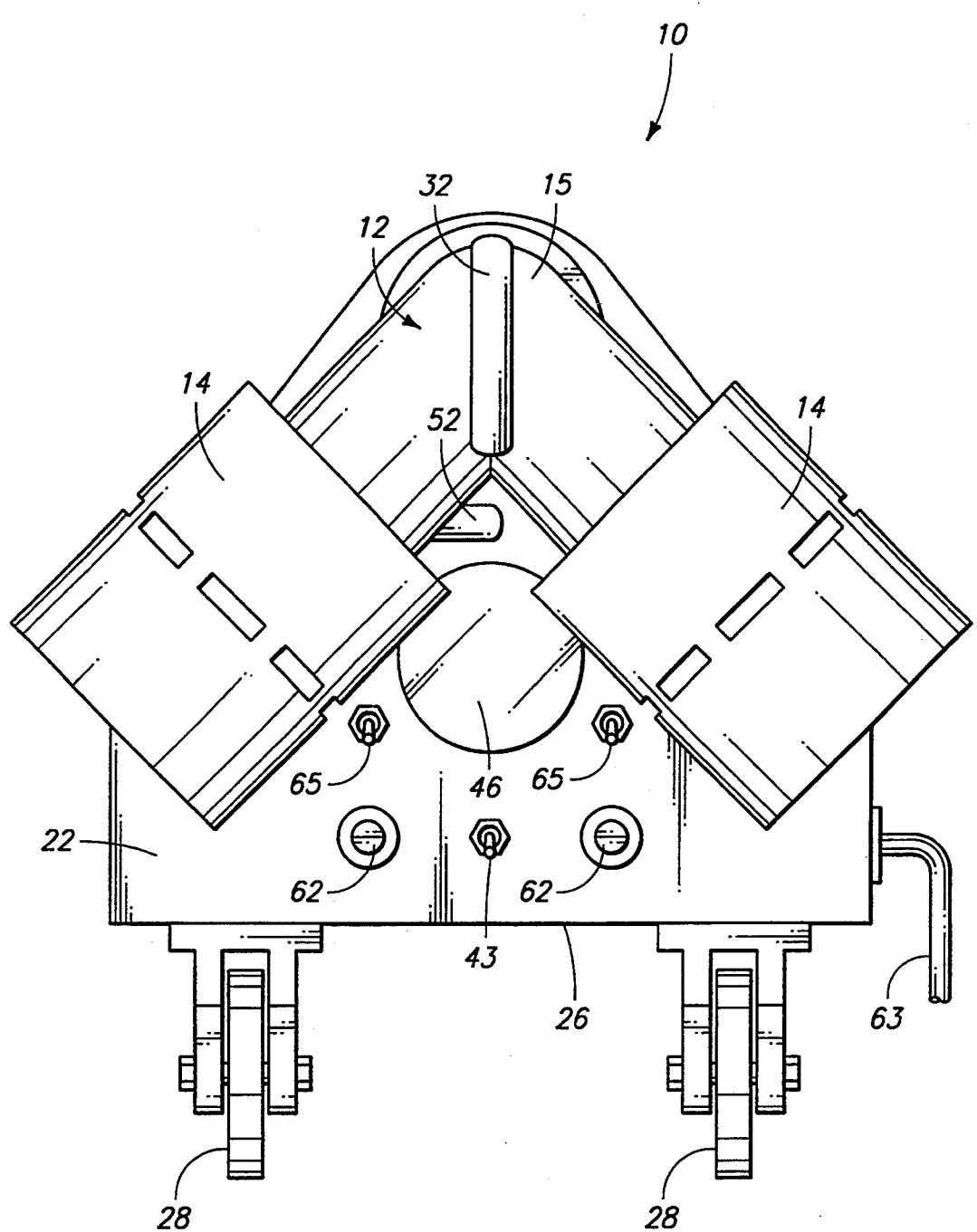
FIG. 2 is a top view of the testing apparatus of FIG. 1.
Figure 3:
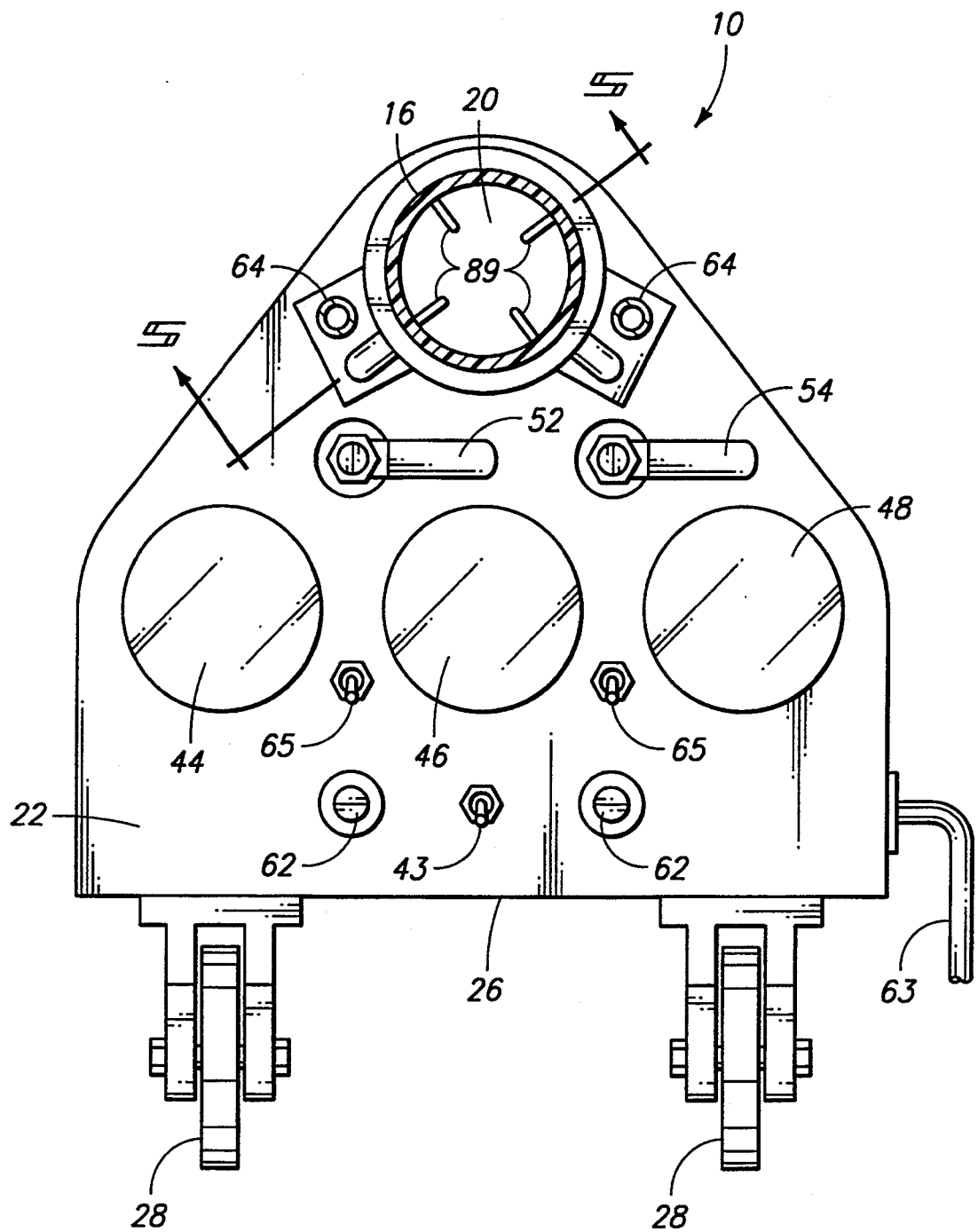
FIG. 3 is a sectional view of the testing apparatus of FIG. 1, taken along the line 3—3 of FIG. 1.
Figure 4:
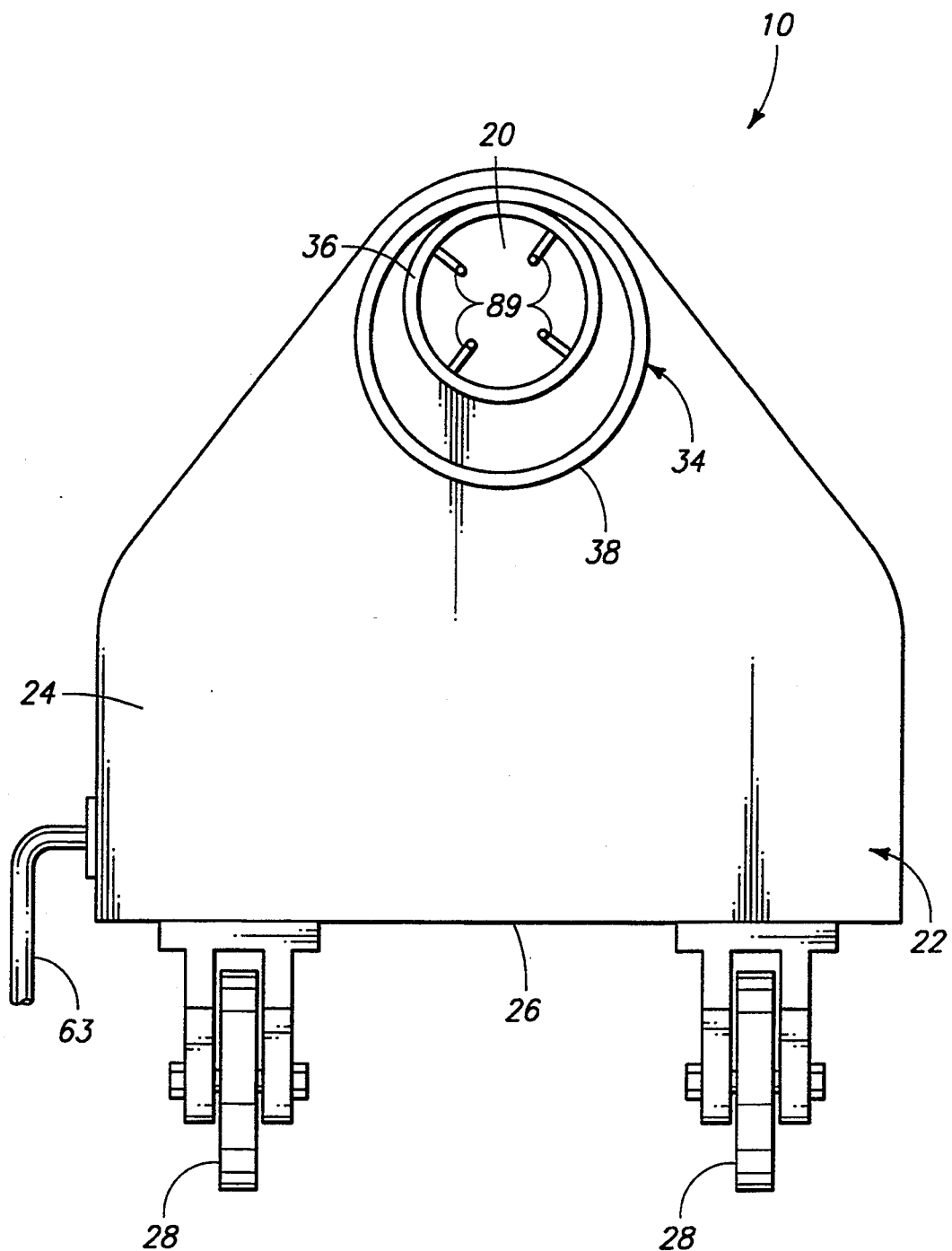
FIG. 4 is a bottom view of the testing apparatus of FIG. 1.

This disclosure of the invention is submitted in furtherance of the constitutional purposes of the U.S. Patent Laws "to promote the progress of science and useful arts." U.S. Constitution, Article 1, Section 8.

FIGS. 1-6 show a preferred embodiment of a testing apparatus in accordance with the invention, generally designated by the reference numeral 10. When used according to the methods described below, testing apparatus 10 is capable of determining the required vacuum characteristics of a radon evacuation system. Particularly, testing apparatus 10 can be used to determine the pressure and volume specifications of a vacuum source which is to be permanently-installed and connected to one or more vent holes in a building basement to remove or evacuate radon from beneath the basement floor.

Figure 6:
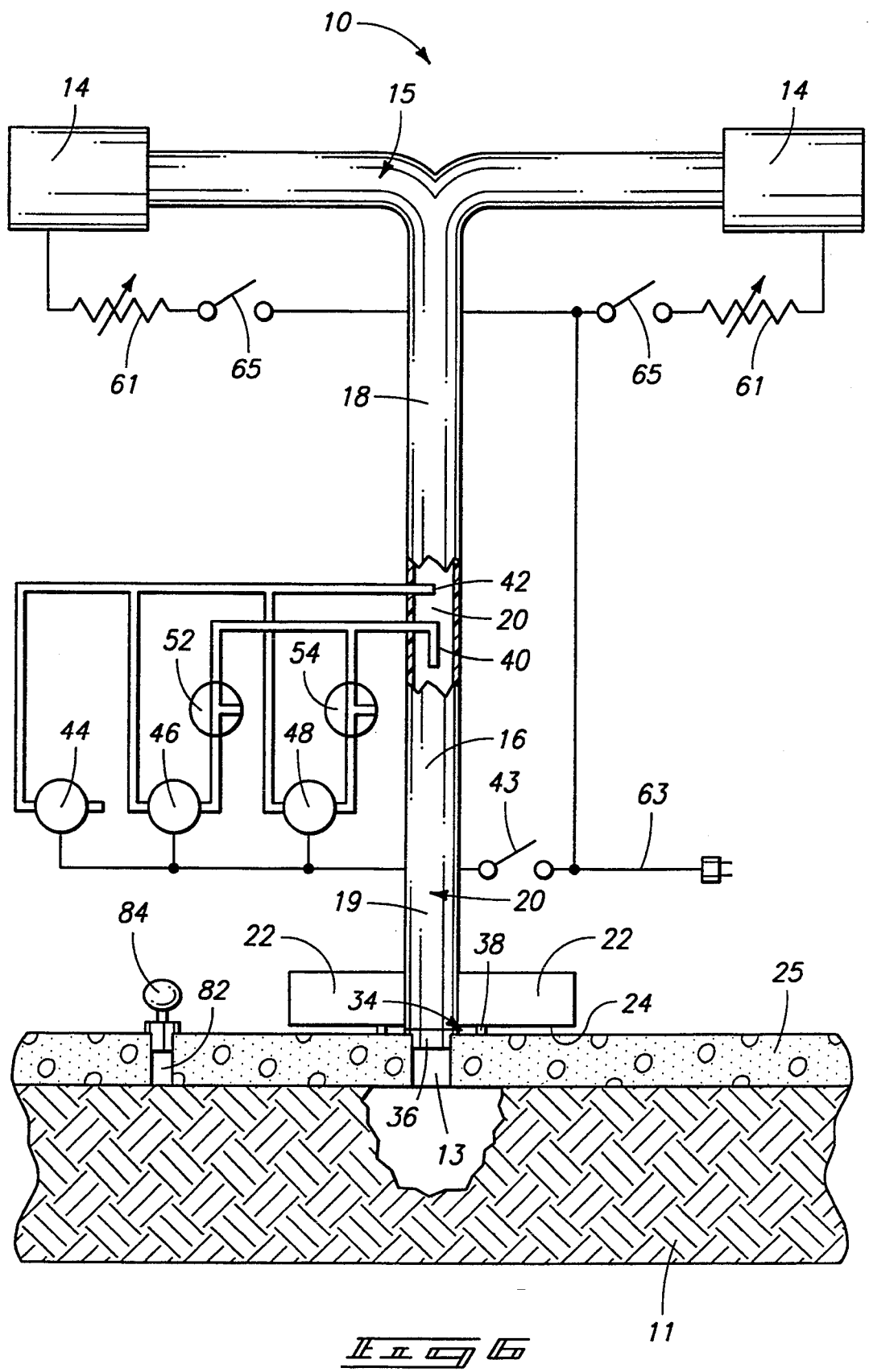
FIG. 6 is a schematic diagram showing the pneumatic and electrical components of the testing apparatus shown in FIG. 1.

Testing apparatus 10 in general comprises a variable or variable-power vacuum test source 12 which can be conveniently mated with a vent hole 13 in a floor of a building's basement. An elongated riser or vacuum tube 16 extends downwardly from vacuum test source 12 for fluid connection to an underfloor ground region 11 through a floor vent hole 13 in a basement floor 25 (FIG. 6).

More specifically, riser 16 extends between a top or source end 18 and a bottom or base end 19, forming an internal vacuum conduit 20 between ends 18 and 19. Vacuum test source 12 is mounted at top end 18 of riser 16 for fluid communication therewith to produce a variable vacuum in and air flow through vacuum conduit 20. The vacuum test source comprises a pair of blowers 14 which include AC brush-type motors. The blowers are connected by a manifold 15 to top end 18 of riser 16. Each blower is capable of producing a static pressure of eighty inches of water column or one hundred cubic feet per minute of air. While two blowers are used in the preferred embodiment for flexibility and convenience, a single larger blower could alternatively be used.

A free-standing base 22 is positioned at the bottom end of riser 16. Testing apparatus 10 includes a vacuum source adjustment means comprising two vacuum source adjustment knobs 62 in base 22. Knobs 62 are electrically connected to regulate blowers 14. Vacuum source adjustment knobs 62 operate corresponding rheostats 61 (FIG. 6) which accept AC power through a power cord 63 and supply variable power to the blower motors through conductors contained in electrical conduits 64. Vacuum source adjustment knobs 62 individually vary the rotational speed and corresponding vacuum production of blowers 14. A pair of power switches 65 in base 22 are electrically positioned to selectively disconnect power from one or both of blowers 14.

While blowers 14 are provided integrally with the testing apparatus shown, an alternative embodiment, not shown, would have a connector at the top end of riser 16 to receive a hose or conduit from an external vacuum source such as a shop-type vacuum cleaner. Although such vacuum cleaners are not typically provided with means for varying their vacuum capacity, said alternative embodiment could include a power receptacle so that the vacuum cleaner could be electrically connected to receive power from the testing apparatus. One of vacuum source adjustment knobs 62 would control power to the power receptacle, thereby allowing control of power to the vacuum cleaner to regulate its capacity.

Base 22 has a lower support surface 24 (FIG. 4) which rests upon basement floor 25 (FIG. 6) to support riser 16 and vacuum test source 12 over and above floor vent hole 13. Base 22 has a front edge 26 and a pair of wheels 28 which extend laterally forward from front edge 26. The wheels are mounted at an appropriate elevation so that they contact the floor only when the apparatus is tipped. A handle 32 is mounted at the top end of riser 16 for grasping by an operator. This allows an operator to easily tip the apparatus onto its wheels so that the apparatus can be moved or rolled on its wheels from one vent hole to another. However, the apparatus rests solidly on the floor when in use.

The bottom end 19 of riser 16 is received through base 22 for fluid communication with vent hole 13. A vent hole adapter 34 (FIG. 4) is formed at bottom end 19 of riser 16, beneath base 22, for fluid communication with vacuum conduit 20. Adapter 34 includes a cylindrical sleeve 36 which extends below lower surface 24 of base 22. It is sized to mate with floor vent hole 13 beneath base 22 to connect vacuum conduit 20 to underfloor ground region 11 adjacent floor vent hole 13. A seal or gasket 38 on lower surface 24 of base 22 surrounds sleeve 36. Seal 38 has a diameter greater than that of floor vent hole 13 so that it surrounds floor vent hole 13 when sleeve 36 is received therein. Seal 38 is thus positioned as a seal between base 22 and the basement floor when testing apparatus 10 is in use.

The base, riser, and manifold are preferably constructed of PVC or ABS plastic. In particular, riser 16 can be fabricated from PVC or ABS tubing such as is commonly available for plumbing purpose.

Testing apparatus 10 includes instrumentation for displaying the static pressure and air volume produced by the vacuum source during testing. More specifically, base 22 contains measurement means for measuring vacuum produced within vacuum conduit 20 by vacuum source 12 and for measuring air flow produced through vacuum conduit 20 by vacuum source 12.

In the preferred embodiment described herein, the measurement means includes a total pressure detection assembly 40 and a static pressure detection assembly 42, both of which are positioned within or along riser 16. These components are positioned along riser 16 in accordance with conventional practice, wherein the distance from the detection assemblies from the top of the riser is at least 7.5 times the internal diameter of the riser, and the distance from the detection assemblies from the bottom of the riser is at least 5 times the internal diameter of the riser.

Figure 5:
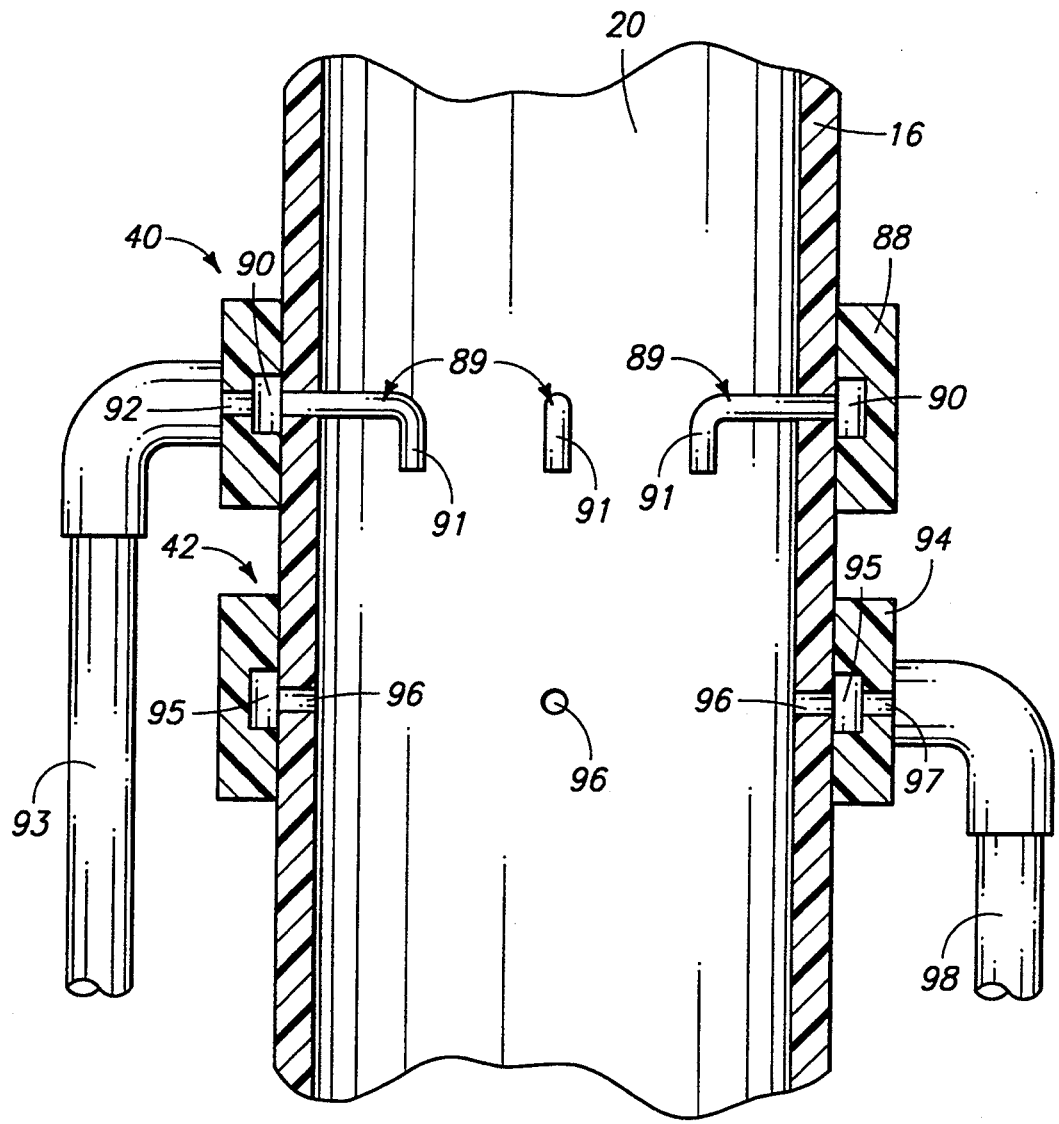
FIG. 5 is a sectional view of the testing apparatus of FIG. 1, taken along the line 5—5 of FIG. 3.

Total pressure detection assembly 40, best shown in FIG. 5, comprises a collar 88 and a plurality of total pressure probes or tubes 89. Collar 88 is received over riser 16. Collar 88 has an internal annular groove or channel 90 which extends completely around collar 88 and which surrounds riser 16. Collar 88 has an internal diameter which is complementary to the external diameter of riser 16 to form a sealing fit between collar 88 and riser 16. Sealing between collar 88 and riser 16 is preferably ensured by using a suitable sealing material or adhesive.

Total pressure probes 89 extend through holes in riser 16 into vacuum conduit 20, providing fluid pressure communication from vacuum conduit 20 into annular channel 90. Total pressure probes 89 are positioned at 90 degree intervals around riser 16. They have downwardly-pointed tips 91 which are horizontally positioned at the centroids of 90 degree quadrants within vacuum conduit 20.

A total pressure measurement aperture 92 extends outward from annular channel 90 through collar 88 to allow connection to pressure measurement devices to be described below. A total pressure measurement tube 93 is connected between pressure measurement aperture 92 and the pressure measurement devices.

Static pressure detection assembly 42 comprises a collar 94. Collar 94 is received over riser 16 below collar 88. Collar 94 has an internal annular groove or channel 95 which extends completely around collar 94 and which surrounds riser 16. Collar 94 has an internal diameter which is complementary to the external diameter of riser 16 to form a sealing fit between collar 94 and riser 16. Sealing between collar 94 and riser 16 is preferably ensured by using a suitable sealing material or adhesive.

Four static pressure communication holes 96 extend through riser 16 at equal 90 degree intervals about vacuum conduit 20 for fluid pressure communication between vacuum conduit 20 and annular channel 95. A static pressure measurement aperture 97 extends outward from annular channel 95 through collar 94 to allow connection to pressure measurement devices to be described below. A static pressure measurement tube 98 is connected between pressure measurement aperture 97 and the pressure measurement devices.

The measurement means also includes pressure measurement or indicating means connected to total pressure detection assembly 40 and static pressure detection assembly 42 for indicating air velocity or volume through vacuum conduit 20 and for indicating vacuum magnitude within vacuum conduit 20. The indicating means preferably comprises a plurality of gauges which are calibrated to indicate different vacuum and air flow ranges. Furthermore, the indicating means of the preferred embodiment includes at least one dual-purpose gauge which is connected to alternatively indicate vacuum in vacuum conduit 20 or air flow through vacuum conduit 20. The gauges are powered through a two-position switch 43. Valved T-connections 99 (FIG. 1) are provided in pressure measurement tubes 93 and 98 to allow independent verification and calibration of the gauges.

The details of the measurement means are best described with reference to FIG. 6. As shown, three separate differential pressure gauges, each having a pair of input ports, are utilized. A first differential pressure gauge 44 has one input port connected to annular channel 95 of static pressure detection assembly 42 and the other input port connected to the atmosphere to measure static pressure within vacuum conduit 20, relative to atmospheric pressure. First pressure gauge 44 has a range of zero to 100 inches of water column.

The remaining two pressure gauges, 46 and 48, are connected through valves 52 and 54, respectively, to indicate either static pressure or air volume. For instance, a second differential gauge 46 has a first input port connected to annular channel 95 of static pressure detection assembly 42. However, a two-position, three-way valve 52 is connected between the second input port of second gauge 46 and annular channel 90 of total pressure detection assembly 40. Valve 52 is operable between first and second positions to alternatively connect the second input port of second gauge 46 to total pressure detection assembly 40 or to ambient atmosphere. Likewise, a third differential pressure gauge 48 has a first input port connected to static pressure detection assembly 42. A valve 54 is connected between the second input port of third gauge 48 and annular channel 90 of total pressure detection assembly 40. Valve 54 is operable between first and second positions to alternatively connect the second input port of second gauge 46 to total pressure detection assembly 40 or to ambient atmosphere.

When differential gauges 46 and 48 are connected between static pressure detection assembly 42 and total pressure detection assembly 40, they respond to velocity pressure (the difference between static pressure and total pressure) within vacuum conduit 20. The velocity pressure is directly proportional to air flow, velocity, and volume through conduit 20. The faces of gauges 46 and 48 have first visual scales which are calibrated to indicate cubic feet per minute.

When differential gauges 46 and 48 are connected between static pressure detection assembly 42 and ambient pressure, they respond to static pressure within vacuum conduit 20. The gauges have second visual scales, indicating static pressure in pounds per square inch, to be used when valves 52 and 54 are operated to disconnect gauges 46 and 48 from total pressure detection assembly 40. These dual-function gauges thus provide alternative indications of both vacuum pressure and air flow.

Gauge 46 is selected to provide air flow measurements in the range of zero to five hundred cubic feet per minute or static pressure of zero to twelve inches of water column. Gauge 48 is selected to provide air flow measurements in the range of zero to two hundred cubic feet per minute or static pressure of zero to one inch of water column.

In actual operation, vacuum source adjustment knobs 62 are used to vary the vacuum produced by vacuum test source 12 and to thereby determine the minimum vacuum and minimum air flow required to create a negative pressure in underfloor ground region 11. The measurement and indicating means described above provide measurements of said minimum vacuum and minimum air flow once vacuum test source 12 has been adjusted to a minimum capacity.

Preliminary operational steps include providing one or more vent holes 13 through a building floor 25 over a ground region 11 which is to be tested for fluid communication. About one cubic foot of earth is typically removed from beneath each vent hole to facilitate optimal fluid or gas communication. A plurality of test holes 82 (only one shown) are also provided at appropriate spaced distances from the vent holes.

Further preliminary steps in accordance with the invention include positioning testing apparatus 10 over floor vent hole 13 so that vacuum test source 12 is connected to ground region 11 through vent hole 13. Such positioning includes mating vent hole adapter 34 with the underlying vent hole 13. Finally, a sensitive vacuum sensing device 84 is placed within one of test holes 82.

Actual testing proceeds by turning on vacuum test source 12, thereby supplying vacuum to ground region 11 through the underlying vent hole. An operator then adjusts the vacuum and corresponding air flow supplied to the ground region through the vent hole by turning or adjusting vacuum source adjustment knobs 62. Further operational steps include measuring pressure beneath the building floor with vacuum sensing device 84, at a single location spaced from the vent hole, while varying the vacuum supplied to the ground region. This spaced location corresponds to test hole 82. All other vent holes are sealed during this step. The preferred methods include adjusting the vacuum to the lowest value which is sufficient to create a negative pressure in ground region 11 at test hole 82. Thus, the vacuum and corresponding air flow are varied until the minimum acceptable vacuum and air flow rate are found, at the lowest blower capacity which produces a negative pressure at test hole 82, as measured by vacuum sensing device 84. After the step of adjusting the vacuum, the minimum acceptable vacuum and air flow are measured by noting the readings of gauges 44, 46, and 48. This provides measurements of the actual static pressure and flow rate at floor vent hole 13. The readings are recorded for subsequent use.

Determining the actual static pressure, after properly adjusting the vacuum source, is accomplished by first observing first static pressure gauge 44. If it reads more than 12 inches of water column, further static pressure measurements are not possible. However, finer measurements of less than 12 inches of water column can be made by observing second gauge 46. Valve 52 should be turned so that gauge 46 indicates static pressure. Even finer measurements of pressures less than one inch of water column can be made by observing third gauge 48 with valve 54 turned so that gauge 46 indicates static pressure.

Determining the actual flow rate is accomplished turning valve 52 so that gauge 46 functions to indicate flow rate. Finer measurements of less than 200 cubic feet per minute can be made with gauge 48 if appropriate.

The procedures above are used to determine the minimum vacuum and flow rate required to produce a negative pressure in each of the plurality of test holes. Results are recorded for each test hole. The procedures are repeated as required for multiple floor vent holes.

The recorded results are used to calculate the required pressure and flow rate of a vacuum source which will be installed in a permanent radon evacuation system. For instance, minimum pressure of such a vacuum source can be determined by noting the highest minimum vacuum reading found during the testing. The corresponding required flow rate can be determined by summing the flow rates noted for each test hole.

Figure 7:
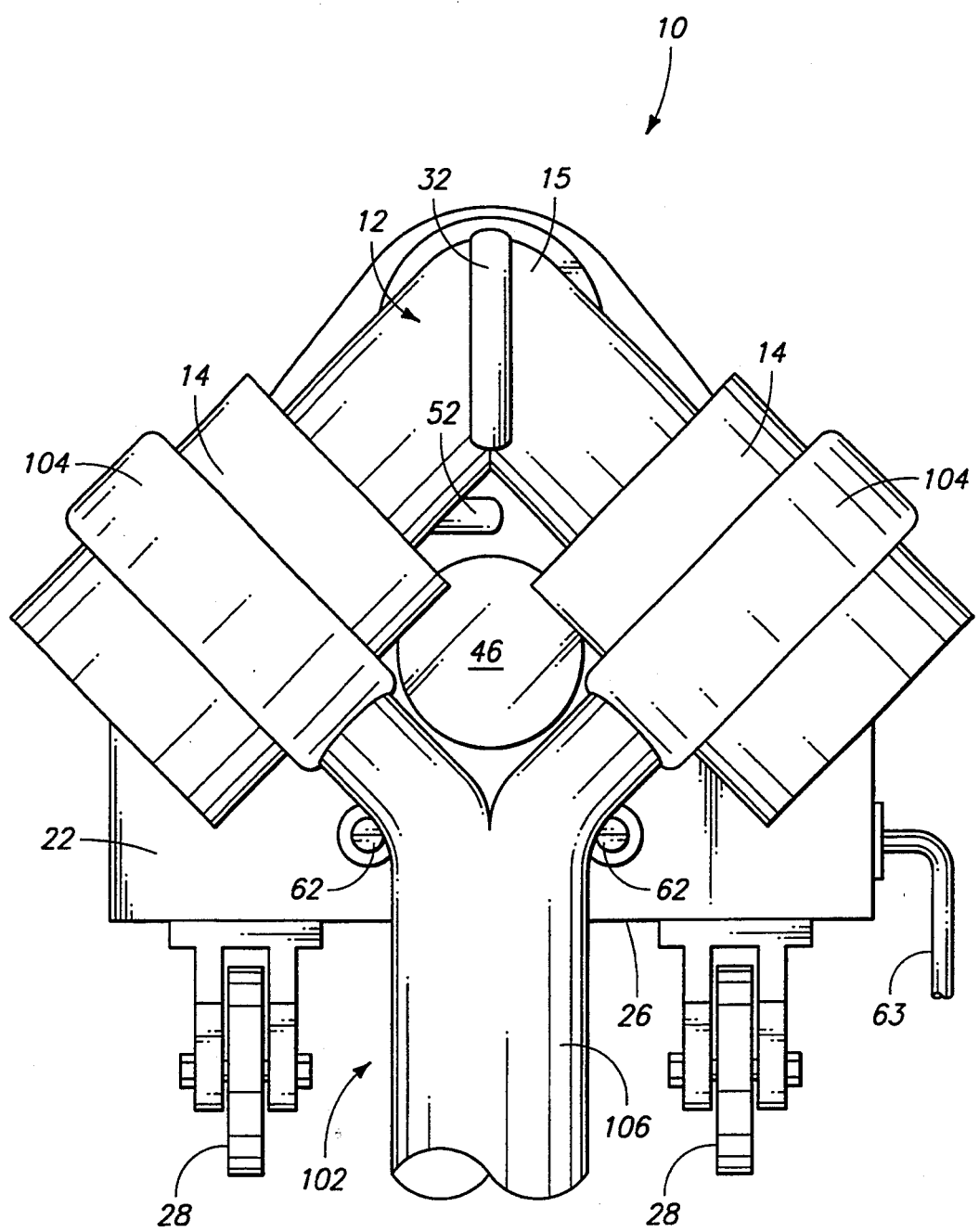
FIG. 7 is a top view of a testing apparatus such as shown in FIG. 1, including a gas exhaust manifold for venting gas which is removed from beneath a basement floor during testing.

FIG. 7 shows testing apparatus 10 with the addition of a gas exhaust manifold 102 for venting gas which is removed from beneath a basement floor during testing. Gas recovery manifold 102 comprises a pair of jackets or sleeves 104 which are placed over or around the air discharge apertures of blowers 14. Jackets 104 are connected to an exhaust conduit 106 to route discharged air outside the building. Gas exhaust manifold 102 allows radon which is removed from beneath a basement floor during testing to be vented to the external atmosphere rather than to the internal atmosphere of the building.

The apparatus and procedures described above allow relatively exact determinations to be made regarding the optimal vacuum capacity of a radon elimination system. Previous testing methods did not provide any such capability. This functionality is provided in a unit which is even more convenient to connect and use than the shop-type vacuum cleaners commonly being used.

In addition, the device described above allows detection of basement floor cracks and other leaks which would probably not have been detected with other systems. A floor crack can provide a source of air to underfloor areas which overcomes any vacuum produced at a nearby vent hole. This makes it impossible to establish a negative pressure at associated test holes, making it appear as if there is no communication between the vent hole and corresponding test holes. Previous testing methods were limited to noting the absence of vacuum at the test holes. The prior art methods provided no way to determine whether the condition was caused by a crack or by an absence of underfloor fluid communication. When using the apparatus and methods above, however, an operator will often note an abnormally high flow rate at any vent hole associated with a floor crack. Once aware of the possibility of a floor crack, an operator can search for the crack. The crack can, in many cases, be repaired. This reduces the flow rate which must be produced by a radon evacuation system, while also reducing the number of vent holes required.

In compliance with the patent laws, the invention has been described in language more or less specific as to structural features. The invention is not, however, limited to the specific features described above. Rather, this specification has disclosed a preferred form of putting the invention into effect. The invention is, therefore, claimed in any of its forms or modifications within the proper scope of the appended claims appropriately interpreted in accordance with the doctrine of equivalents.

I claim:

1. A testing apparatus for use with a vacuum test source to determine required vacuum characteristics of a radon evacuation system, the radon evacuation system being of a type which utilizes floor vent holes in a basement floor to evacuate radon from beneath the basement floor, the apparatus comprising:

a vacuum conduit having a base end and a source end for connection between a floor vent hole and said vacuum test source;

measurement means for measuring vacuum produced within the vacuum conduit by said vacuum test source;

a vacuum test source adjustment which is operably connected to regulate the vacuum test source to provide the minimum vacuum required to create a negative pressure in a region under the basement floor, said region extending to points remote from the floor vent hole, the measurement means providing a measurement of said minimum vacuum.

2. A testing apparatus as recited in claim 1 and further comprising a free-standing base which supports the vacuum conduit above said floor vent hole.

3. A testing apparatus as recited in claim 1 and further comprising a free-standing base which supports the vacuum conduit above said floor vent hole, wherein the measurement means comprises at least one gauge for measuring static pressure and flow rate.

4. A testing apparatus as recited in claim 1 wherein the measurement means is further for measuring flow rate produced through the vacuum conduit by said vacuum test source, the measurement means comprising a plurality of gauges which are calibrated to indicate different vacuum and flow rate ranges.

5. A testing apparatus as recited in claim 1 wherein the measurement means is further for measuring flow rate produced through the vacuum conduit by said vacuum test source, the measurement means comprising at least one dual-purpose gauge which is connected to alternatively indicate vacuum in the vacuum conduit or flow rate through the vacuum conduit.

6. A testing apparatus as recited in claim 1 wherein the measurement means is further for measuring flow rate produced through the vacuum conduit by said vacuum test source, the measurement means comprising:
 a total pressure detection assembly positioned along the vacuum conduit;
 a static pressure detection assembly positioned along the vacuum conduit;
 a differential pressure gauge connected to the total pressure detection assembly and the static pressure detection assembly to indicate flow rate through the vacuum conduit.

7. A testing apparatus as recited in claim 1 wherein the measurement means is further for measuring flow rate produced through the vacuum conduit by said vacuum test source, the measurement means comprising:
 a differential pressure gauge having two ports;
 a static pressure detection assembly positioned along the vacuum conduit, the static pressure detection assembly being connected to a first of the differential pressure gauge ports;
 a total pressure detection assembly positioned along the vacuum conduit;
 a valve which is connected between the total pressure detection assembly and a second of the differential pressure gauge ports, the valve being operable to alternatively connect the second differential pressure gauge port to the total pressure detection assembly or to ambient atmosphere.

8. A testing apparatus for determining required vacuum characteristics of a radon evacuation system, the radon evacuation system being of a type which utilizes floor vent holes in a basement floor to evacuate radon from beneath the basement floor, comprising:
 an elongated vacuum tube which extends from a base end to a source end;
 a variable-power vacuum test source mounted at the source end of the vacuum tube for fluid communication therewith to produce a variable vacuum in the vacuum tube;
 a base at the base end of the elongated vacuum tube to support the vacuum tube and the vacuum test source above a floor vent hole;
 a vent hole adapter formed beneath the base in fluid communication with the vacuum tube to connect the vacuum tube to an underfloor ground region through the floor vent hole;
 measurement means for measuring vacuum produced within the vacuum tube by the vacuum test source and for measuring flow rate produced through the vacuum tube by the vacuum test source;
 a vacuum test source adjustment which is operably connected to regulate the vacuum test source to provide minimum vacuum and minimum flow rate required to create a negative pressure in a region under the basement floor, said region extending to points remote from the floor vent hole, the measurement means providing measurements of the minimum vacuum and minimum flow rate.

9. A testing apparatus as recited in claim 8 wherein the measurement means comprises a plurality of gauges which are calibrated to indicate different vacuum and flow rate ranges.

10. A testing apparatus as recited in claim 8 wherein the measurement means comprises at least one dual-purpose gauge which is connected to alternatively indicate vacuum in the vacuum tube or flow rate through the vacuum tube.

11. A testing apparatus as recited in claim 8 wherein the measurement means comprises:
 a total pressure detection assembly positioned along the vacuum tube;
 a static pressure detection assembly positioned along the vacuum tube;
 a differential pressure gauge connected to the total pressure detection assembly and to the static pressure detection assembly.

12. A testing apparatus as recited in claim 8 wherein the measurement means comprises:
 a differential pressure gauge having two ports;
 a static pressure detection assembly positioned along the vacuum tube, the static pressure detection assembly being connected to a first of the differential pressure gauge ports;
 a total pressure detection assembly positioned along the vacuum tube;
 a valve which is connected between the total pressure detection assembly and a second of the differential pressure gauge ports, the valve being operable to alternatively connect the second differential pressure gauge port to the total pressure detection assembly or to ambient atmosphere.

13. A testing apparatus as recited in claim 8, wherein the base has wheels which contact the floor when the testing apparatus is tipped for transport.

14. A testing apparatus as recited in claim 8 and further comprising:
 a pair of wheels extending from the base;
 a handle at the source end of the elongated vacuum tube for grasping by an operator to tip the testing apparatus, wherein the wheels contact the floor when the testing apparatus is tipped to allow the testing apparatus to be transported on the wheels.

15. A testing apparatus for determining required vacuum characteristics of a radon evacuation system, the radon evacuation system being of a type which utilizes floor vent holes in a basement floor to evacuate radon from beneath the basement floor, comprising:
 an elongated riser extending from a bottom end to a top end, the elongated riser forming a vacuum conduit between its ends;
 a vent hole adapter at the bottom end of the elongated riser, the vent hole adapter being sized to mate with a floor vent hole to connect the vacuum conduit of the elongated riser to an underfloor ground region adjacent the floor vent hole;
 a variable-power vacuum test source mounted at the top end of the elongated riser for fluid communication with the vacuum conduit to produce a variable vacuum in the vacuum conduit and a variable flow rate through the vacuum conduit;
 a total pressure detection assembly positioned along the riser;

a static pressure detection assembly positioned along the riser;

indicating means connected to the total pressure detection assembly and the static pressure detection assembly for indicating flow rate through the vacuum conduit and for indicating vacuum within the vacuum conduit;

a vacuum test source adjustment which is operably connected to regulate the vacuum test source to provide minimum vacuum and minimum flow rate required to create a negative pressure in a region under the basement floor, said region extending to points remote from the floor vent hole, the indicating means allowing the minimum vacuum and minimum flow rate to be recorded.

16. A testing apparatus as recited in claim 15 and further comprising a base which supports the riser and the vacuum test source above the floor vent hole, the vent hole adapter being formed beneath the base.

17. A testing apparatus as recited in claim 15 wherein the indicating means comprises a plurality of gauges which are calibrated to indicate different vacuum and flow rate ranges.

18. A testing apparatus as recited in claim 15 wherein the indicating means comprises at least one dual-purpose gauge which is connected to alternatively indicate vacuum in the vacuum conduit or flow rate through the vacuum conduit.

19. A testing apparatus as recited in claim 15 wherein the indicating means comprises a differential pressure gauge connected to the total pressure detection assembly and the static pressure detection assembly.

20. A testing apparatus as recited in claim 15 wherein the indicating means comprises a differential pressure gauge having two ports, the static pressure detection assembly being connected to a first of the differential pressure gauge ports, the testing apparatus further comprising a valve which is connected between the total pressure detection assembly and a second of the differential pressure gauge ports, the valve being operable to alternatively connect the second differential pressure gauge port to the total pressure detection assembly or to ambient atmosphere.

21. A testing apparatus as recited in claim 15 and further comprising a base which supports the riser and the vacuum test source above the floor vent hole, the base having wheels which contact the floor when the testing apparatus is tipped for transport.

22. A testing apparatus as recited in claim 15 and further comprising:

a base which supports the riser and the vacuum test source above the floor vent hole;

a pair of wheels extending from the base;

a handle at the top end of the elongated riser for grasping by an operator to tip the testing apparatus, wherein the wheels contact the floor when the testing apparatus is tipped to allow the testing apparatus to be transported on the wheels.

23. A testing method of testing for fluid communication throughout a ground region beneath a building floor to determine required vacuum characteristics of a radon evacuation system, the method comprising:

providing a vent hole through the building floor over the ground region;

supplying vacuum to the ground region through the vent hole;

measuring pressure beneath the building floor at a spaced distance from the vent hole;

adjusting the vacuum supplied to the ground region through the vent hole to a minimum value which is sufficient to create a negative pressure in the ground region at the spaced distance from the vent hole; and measuring the vacuum supplied to the ground region through the vent hole after said step of adjusting the vacuum.

24. A testing method as recited in claim 23 and further comprising the step of measuring flow rate through the vent hole after said step of adjusting the vacuum.

25. A testing method as recited in claim 23 and further comprising the step of recording vacuum and flow rate at the vent hole after said step of adjusting the vacuum.

* * * * *